(12) United States Patent
Waku et al.

(10) Patent No.: US 9,788,729 B2
(45) Date of Patent: Oct. 17, 2017

(54) IMAGE PROCESSING APPARATUS AND IMAGE PROCESSING METHOD

(75) Inventors: Toshiya Waku, Yaita (JP); Hitoshi Yamagata, Otawara (JP)

(73) Assignee: TOSHIBA MEDICAL SYSTEMS CORPORATION, Tochigi (JP)

( * ) Notice: Subject to any disclaimer, the term of this patent is extended or adjusted under 35 U.S.C. 154(b) by 1109 days.

(21) Appl. No.: 12/621,179

(22) Filed: Nov. 18, 2009

(65) Prior Publication Data

US 2010/0128963 A1 May 27, 2010

(30) Foreign Application Priority Data

Nov. 21, 2008 (JP) ................................. 2008-298534

(51) Int. Cl.

| | |
|---|---|
| G06K 9/00 | (2006.01) |
| A61B 5/00 | (2006.01) |
| A61B 5/02 | (2006.01) |
| G06T 11/00 | (2006.01) |
| G06T 15/08 | (2011.01) |
| G06T 19/00 | (2011.01) |

(52) U.S. Cl.
CPC ........ *A61B 5/0073* (2013.01); *A61B 5/02007* (2013.01); *G06T 11/008* (2013.01); *G06T 15/08* (2013.01); *G06T 19/00* (2013.01); *G06T 2211/404* (2013.01)

(58) Field of Classification Search
CPC ....... A61B 8/0891; A61B 6/504; A61B 34/20; A61B 5/02007
USPC ......... 382/128–131, 154, 134; 600/425, 443, 600/407, 504, 447
See application file for complete search history.

(56) References Cited

U.S. PATENT DOCUMENTS

| | | | | |
|---|---|---|---|---|
| 4,945,478 A | * | 7/1990 | Merickel et al. ............. | 382/131 |
| 5,148,809 A | * | 9/1992 | Biegeleisen-Knight et al. .............................. | 600/443 |
| 6,674,894 B1 | * | 1/2004 | Parker et al. .................. | 382/154 |
| 6,842,638 B1 | * | 1/2005 | Suri et al. ...................... | 600/425 |
| 7,369,691 B2 | * | 5/2008 | Kondo .................... | G06T 15/08 382/128 |
| 7,488,292 B2 | * | 2/2009 | Adachi ......................... | 600/504 |

(Continued)

FOREIGN PATENT DOCUMENTS

| | | | | | |
|---|---|---|---|---|---|
| EP | | 0981109 A2 | * | 8/1999 | ............. G06T 17/40 |
| JP | | 2004-230086 A | | 8/2004 | |

(Continued)

OTHER PUBLICATIONS

Japanese Office Action with its English Translation for Japanese Patent Application No. 2009-263182 mailed on Oct. 8, 2013.

*Primary Examiner* — Victoria P Shumate
*Assistant Examiner* — Teresa Williams
(74) *Attorney, Agent, or Firm* — Kenichiro Yoshida

(57) ABSTRACT

A storage unit stores volume data including a blood vessel region. An extracting unit extracts the blood vessel region from the volume data. A specifying unit specifies a position of a region of interest in the blood vessel region and a deflection direction of a blood vessel region included in the region of interest. A determining unit determines a viewing position and a viewing direction based on the position of the region of interest and the deflection direction. A generating unit generates image data concerning the viewing position and the viewing direction based on the volume data. A display unit displays an image represented by the image data.

18 Claims, 8 Drawing Sheets

At the initial viewing position and at the initial viewing direction, stenosis part 53 may not be confirmed in the image

(56) References Cited

U.S. PATENT DOCUMENTS

| | | | |
|---|---|---|---|
| 7,529,396 B2* | 5/2009 | Matsumoto | G06T 15/08 128/922 |
| 7,835,500 B2* | 11/2010 | Fu | G06T 7/0026 128/922 |
| 7,890,156 B2* | 2/2011 | Ooi et al. | 600/425 |
| 7,912,269 B2* | 3/2011 | Ikeda et al. | 382/131 |
| 7,970,193 B2* | 6/2011 | Rouet | G06T 7/0012 382/131 |
| 8,090,176 B2* | 1/2012 | Kinnstaetter et al. | 382/130 |
| 8,150,113 B2* | 4/2012 | Ray | G06T 7/0012 128/920 |
| 8,428,317 B2* | 4/2013 | Kimia | G06T 7/0012 382/128 |
| 2002/0068863 A1* | 6/2002 | Slack | 600/407 |
| 2006/0246358 A1* | 11/2006 | Ryan | A61F 9/008 430/5 |
| 2008/0101667 A1* | 5/2008 | Begelman | A61B 5/02007 382/128 |
| 2008/0101674 A1* | 5/2008 | Begelman | G06K 9/3241 382/130 |
| 2008/0118126 A1 | 5/2008 | Sakaguchi | |
| 2010/0067753 A1* | 3/2010 | Visser | A61B 5/02007 382/128 |
| 2010/0099961 A1* | 4/2010 | Hubner et al. | 600/322 |

FOREIGN PATENT DOCUMENTS

| | | |
|---|---|---|
| JP | 2005-198708 A | 7/2005 |
| JP | 2006-167287 A | 6/2006 |
| JP | 2006-246941 A | 9/2006 |
| JP | 2008-067991 A | 3/2008 |
| JP | 2008-125736 A | 6/2008 |
| JP | 2008-126070 A | 6/2008 |
| JP | 2008-188428 A | 8/2008 |

* cited by examiner

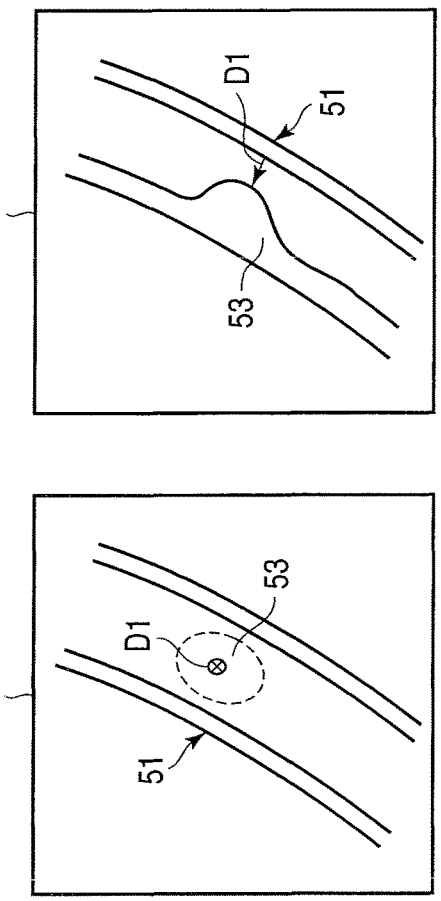
FIG. 5
Swelling of stenosis part 531 cannot be confirmed in image
FIG. 6
Swelling of stenosis part 532 can be confirmed in image
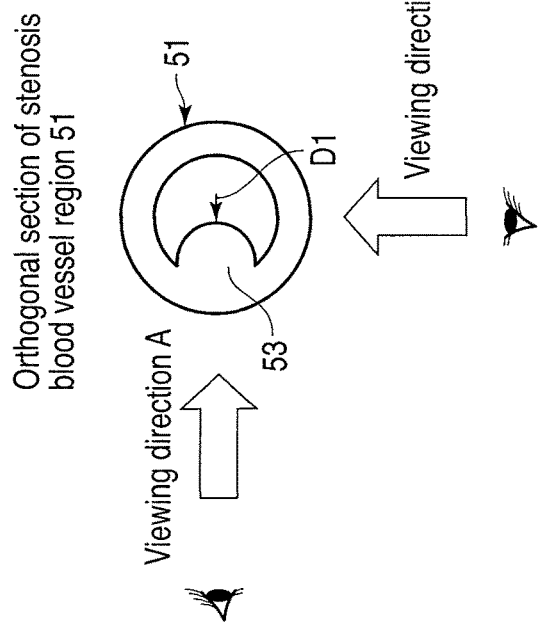
FIG. 4

IMAGE PROCESSING APPARATUS AND IMAGE PROCESSING METHOD

CROSS-REFERENCE TO RELATED APPLICATIONS

This application is based upon and claims the benefit of priority from prior Japanese Patent Application No. 2008-298534, filed Nov. 21, 2008, the entire contents of which are incorporated herein by reference.

BACKGROUND OF THE INVENTION

1. Field of the Invention

The present invention relates to an image processing apparatus and an image processing method for use in image diagnosis of lesion parts in blood vessels.

2. Description of the Related Art

In recent years, various techniques have been developed for image processing apparatuses that are designed for image diagnosis of lesion parts in blood vessels, particularly lesion parts in coronary artery. These techniques include, for example, (1) extraction of images of the heart or the coronary artery (see, for example, Jpn. Pat. Appln. KOKAI Publication No. 2004-230086 and Jpn. Pat. Appln. KOKAI Publication No. 2006-246941); (2) labeling and classification of the branches of the coronary artery (see, for example, Jpn. Pat. Appln. KOKAI Publication No. 2004-283373); (3) detection and display of constricted parts (see, for example, Jpn. Pat. Appln. KOKAI Publication No. 2004-283373, Jpn. Pat. Appln. KOKAI Publication No. 2005-198708, Jpn. Pat. Appln. KOKAI Publication No. 2006-167287, Jpn. Pat. Appln. KOKAI Publication No. 2006-246941, Jpn. Pat. Appln. KOKAI Publication No. 2008-67991, Jpn. Pat. Appln. KOKAI Publication No. 2008-125616, and Jpn. Pat. Appln. KOKAI Publication No. 2008-125736); and (4) assistance in preparing clinical reports and clinical charts.

The technique (1), i.e., extracting images of the coronary artery, is no more than extracting the entire image of the object of interest. The technique (2), i.e., labeling, is indeed useful in automating the labeling annotation of the respective blood-vessel branches. However, this technique inevitably labels the blood-vessel branches of non-interest, too. The technique therefore requires a manual edition. The technique (3), i.e., detection and display of the constricted part, cannot accomplish the display of the clinical reports or clinical charts about the constriction of a blood vessel. The technique (4), i.e., assistance in preparing the clinical reports and clinical charts, needs manual selection of the blood vessel of interest or the lesion part (mainly, the constricted part) and manual setting of various conditions such as viewing direction and label positions. Consequently, it requires cumbersome operations to prepare clinical reports and clinical charts.

BRIEF SUMMARY OF THE INVENTION

An object of this invention is to provide an image processing apparatus and an image processing method, both capable of increasing the efficiency of image diagnosis of lesion parts of blood vessels.

According to a first aspect of the present invention, an image processing apparatus includes: a storage unit configured to store volume data including a blood vessel region; an extracting unit configured to extract the blood vessel region from the volume data; a specifying unit configured to specify a position of a region of interest in the blood vessel region and a deflection direction of a blood vessel region included in the region of interest; a determining unit configured to determine a viewing position and a viewing direction based on the position of the region of interest and the deflection direction; a generating unit configured to generate image data concerning the viewing position and the viewing direction based on the volume data; and a display unit configured to display an image represented by the image data.

According to a second aspect of the present invention, an image processing method includes: extracting a blood vessel region from volume data; specifying a position of a region of interest in the blood vessel region and a deflection direction of a blood vessel region included in the region of interest; determining a viewing position and a viewing direction based on the position of the region of interest and the deflection direction; generating image data concerning the viewing position and the viewing direction based on the volume data; and displaying an image represented by the image data.

Additional objects and advantages of the invention will be set forth in the description which follows, and in part will be obvious from the description, or may be learned by practice of the invention. The objects and advantages of the invention may be realized and obtained by means of the instrumentalities and combinations practically pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a diagram explaining Step S5 shown in FIG. 2, illustrating the relation between the swelling direction and the viewing direction;

FIG. 5 is a diagram explaining Step S5 shown in FIG. 2, illustrating an image concerning the viewing direction A shown in FIG. 4;

FIG. 6 is a diagram explaining Step S5 shown in FIG. 2, illustrating an image concerning the viewing direction B shown in FIG. 4;

DETAILED DESCRIPTION OF THE INVENTION

An image processing apparatus and an image processing method, both according to an embodiment of this invention, will be described with reference to the accompanying drawings. The image processing apparatus and image processing method, according to the embodiment, are applied to the image diagnosis of lesion parts of blood vessels. The blood vessels may exist in any parts of the human body, such as the heart and the brain. For the convenience of explanation, however, the following description relates to the blood vessels in the heart, because the images concerning the heart are believed to be diagnosed well by the technique according to this embodiment.

Figure 1:
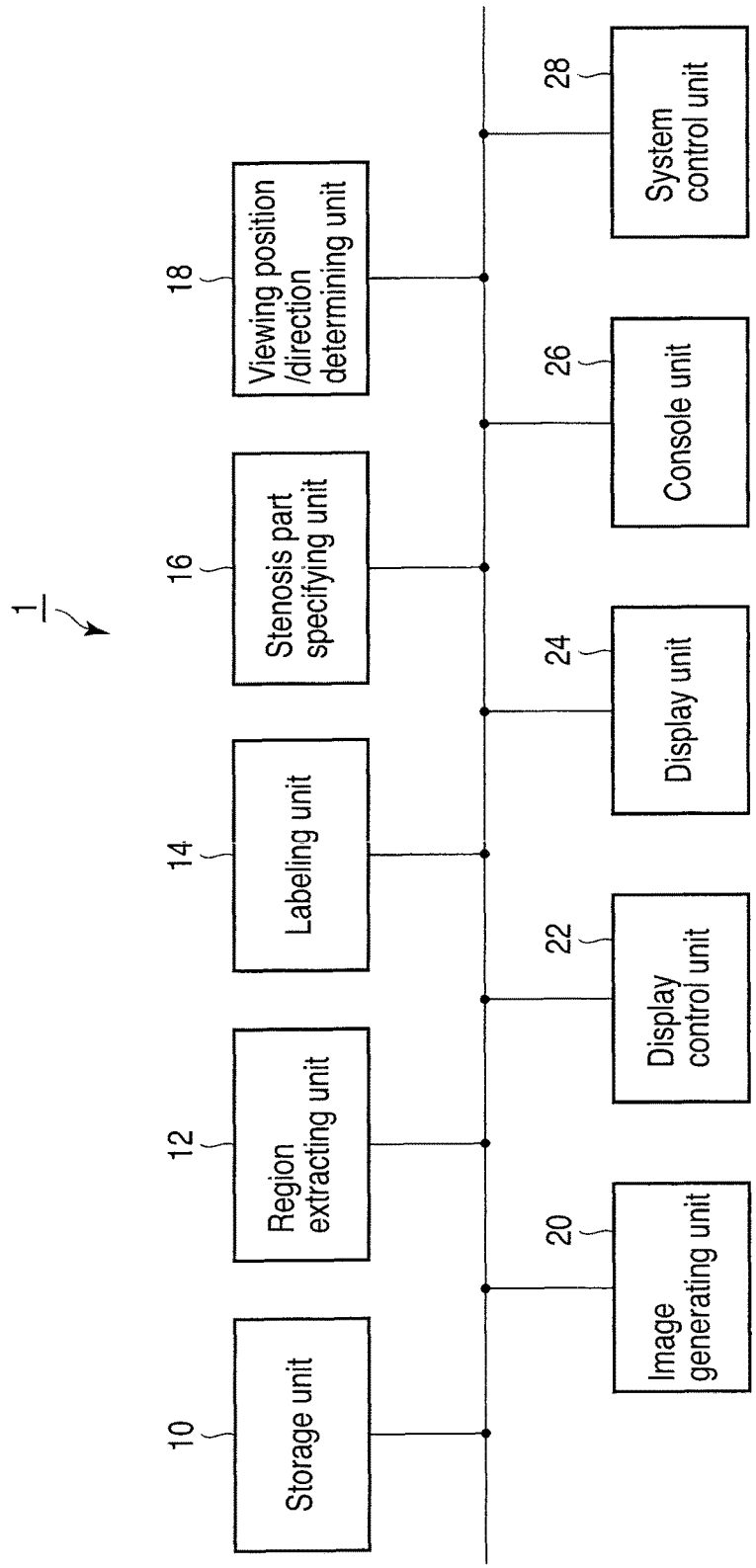
FIG. 1 is a diagram showing the configuration of an image processing apparatus according to an embodiment of the present invention.

FIG. 1 is a diagram showing the configuration of an image processing apparatus 1 according to an embodiment of this invention. As shown in FIG. 1, the image processing apparatus 1 includes a storage unit 10, a region extracting unit 12, a labeling unit 14, a stenosis part specifying unit 16, a viewing position/direction determining unit 18, an image generating unit 20, a display control unit 22, a display unit 24, a console unit 26, and a system control unit 28.

The storage unit 10 stores time-series volume data concerning the heart of a subject. Assume that the coronary artery has its wall deformed due to a plaque or aneurysm. The coronary artery branches from the ascending aorta and extends like a crown on the surface of the heart. The coronary artery branches into the left coronary artery and the right coronary artery. The left coronary artery is classified into left main trunk (LM or LMT), left anterior-descending coronary artery (LAD), and left circumflex coronary artery (LCX). The time-series volume data has been generated through the repeated use of an image diagnosing apparatus such as X-ray computed tomography apparatus, magnetic resonance imaging (MRI) apparatus, ultrasonic diagnosing apparatus, gamma camera, single-photon emission computed tomography (SPECT) apparatus or positron emission tomography (PET) apparatus. The generated volume data is supplied via a network or a storage medium and stored in the storage unit 10. To facilitate the explanation, the volume data is assumed to have been generated by an X-ray computed tomography apparatus. That is, a contrast medium has been injected into the subject and applied to the blood vessel region included in the volume data. The storage unit 10 stores a dedicated program. The dedicated program is used by the system control unit 28 to perform an optimal display process for the lesion part as will be described later.

The region extracting unit 12 extracts the hear region and the blood vessel region from the volume data, by performing a process that uses, for example, threshold values. The blood vessel region is concerned with the coronary artery in the heart. The blood vessel region includes at least one lesion part.

The labeling unit 14 analyzes the structure of the blood vessel region and isolates the blood vessel branches existing in the blood vessel region. The labeling unit 14 then allocates to the branches the codes representing blood vessel labels indicating the anatomical classes of the branches. The stenosis part specifying unit 16 specifies the position of a region of interest in the blood vessel region and the deflection direction of a blood vessel region existing in the region of interest.

The term of "region of interest," used here, means a region that in image diagnosis the user wants to observe. The region of interest is, for example, a lesion part or a lesion suspicion part. The lesion part is already affected. The lesion suspicion part is likely affected. An example of a lesion part of the coronary artery is a part swelled due to a plaque. The wall of the lesion part swells toward the axis of the blood vessel. The deflection direction of the region of interest is the direction in which the blood vessel region is deflected due to the shape change characteristic of the lesion part or lesion suspicion part. In case the lesion part is a stenosis part, the "deflection direction" means the direction in which the blood vessel swells. The stenosis part specifying unit 16 specifies the position of the region of interest and the deflection direction from a parameter (hereinafter called deflection parameter). This parameter indicates the degree of deflection of the blood vessel wall. The deflection parameter used in the present embodiment can be, for example, any parameter already prepared and showing the degree of deflection of the blood vessel wall. The parameter used is, for example, the diameter of the blood vessel existing in the blood vessel region, the stenosis ratio, or the arteriosclerosis index. As known in the art, the stenosis ratio can be calculated by two methods. In one method, the ratio is calculated from the diameter of the blood vessel. In the other method, the ratio is calculated from the section area of the blood vessel region. Either method can be used in this embodiment. The stenosis ratio based on the blood vessel diameter, for example, is defined as the ratio between the diameter of the normal part in the blood vessel region and the diameter of the lesion part of the blood vessel. As well known in the art, the arteriosclerosis index is defined as the ratio of the outside diameter of a blood vessel to the inside diameter of the blood vessel, i.e., outside diameter/inside diameter.

The viewing position/direction determining unit 18 determines the viewing position and the viewing direction from the specified position of the region of interest and the specified deflection direction.

The image generating unit 20 generates image data from the volume data based on the determined viewing direction and the determined viewing position. More precisely, the image generating unit 20 performs a 3-dimensional imaging process on the volume data, thus generating the image data. The 3-dimensional imaging process may be multiplanar reconstruction (MPR), curved planar reconstruction (CPR), stretched CPR (SPR), volume rendering, surface rendering, or maximum intensity projection (MIP). The user of the apparatus 1 can select one of these 3-dimensional imaging processes by operating the console unit 26.

The display control unit 22 controls the display unit 24 to display an image in a prescribed layout in accordance with display conditions. The display conditions include the viewing position, viewing direction, opacity, color, window level, window width, enlargement ratio, type of 3-dimensional imaging process, etc. The user can set these display conditions by operating the console unit 26. Further, the display control unit 22 performs a label display/non-display determining process, a label displaying process, a label-display changing process, and a template display process.

In the label display/non-display determining process, the display control unit 22 determines whether a blood vessel label must be displayed on the displayed image, in accordance with the length ratio between the blood vessel region displayed and the blood vessel region represented by the volume data. The "blood vessel label" is a kind of annotation, which shows the anatomical class of a blood vessel branch.

In the label displaying process, the display control unit 22 may determine that a blood vessel label should be displayed. In this case, the unit 22 arranges the blood vessel label at the displayed image.

In the label-display changing process, the display control unit 22 changes at least one of the size, color and font of the blood vessel label displayed at the image, in accordance with the positional relation the blood vessel label and the blood vessel region have in the displayed image.

In the template display process, the display control unit 22 causes the display unit 24 to display a blood-vessel label template. Using the blood-vessel label template, the user may correct blood vessel labels or may make additional blood vessel labels as he or she operates the console unit 26. The user can move the template to any desirable position, merely by operating the console unit 26.

The display unit 24 can be any display device available, such as a CRT display, a liquid crystal display, or a plasma display.

The console unit 26 inputs display conditions, various instructions and information in accordance with the user's instructions. The console unit 26 can be a pointing device such as a mouse or a track ball, a selecting device such as a mode switch, or an input device such as a keyboard.

The system control unit 28 reads the dedicated program from the storage unit 10 and develops the program in a memory, thereby controlling the other components of the image processing apparatus 1. An optimal process of displaying the lesion part, which characterizes this embodiment, is thereby performed.

An exemplary clinical use of the optimal process of displaying the lesion part, according to this embodiment, will be explained below in detail. The following explanation is based on the assumption that the region of interest is a lesion part, and that the position of the region of interest and the deflection direction are therefore the position of the stenosis part and swelling direction, respectively.

Figure 2:
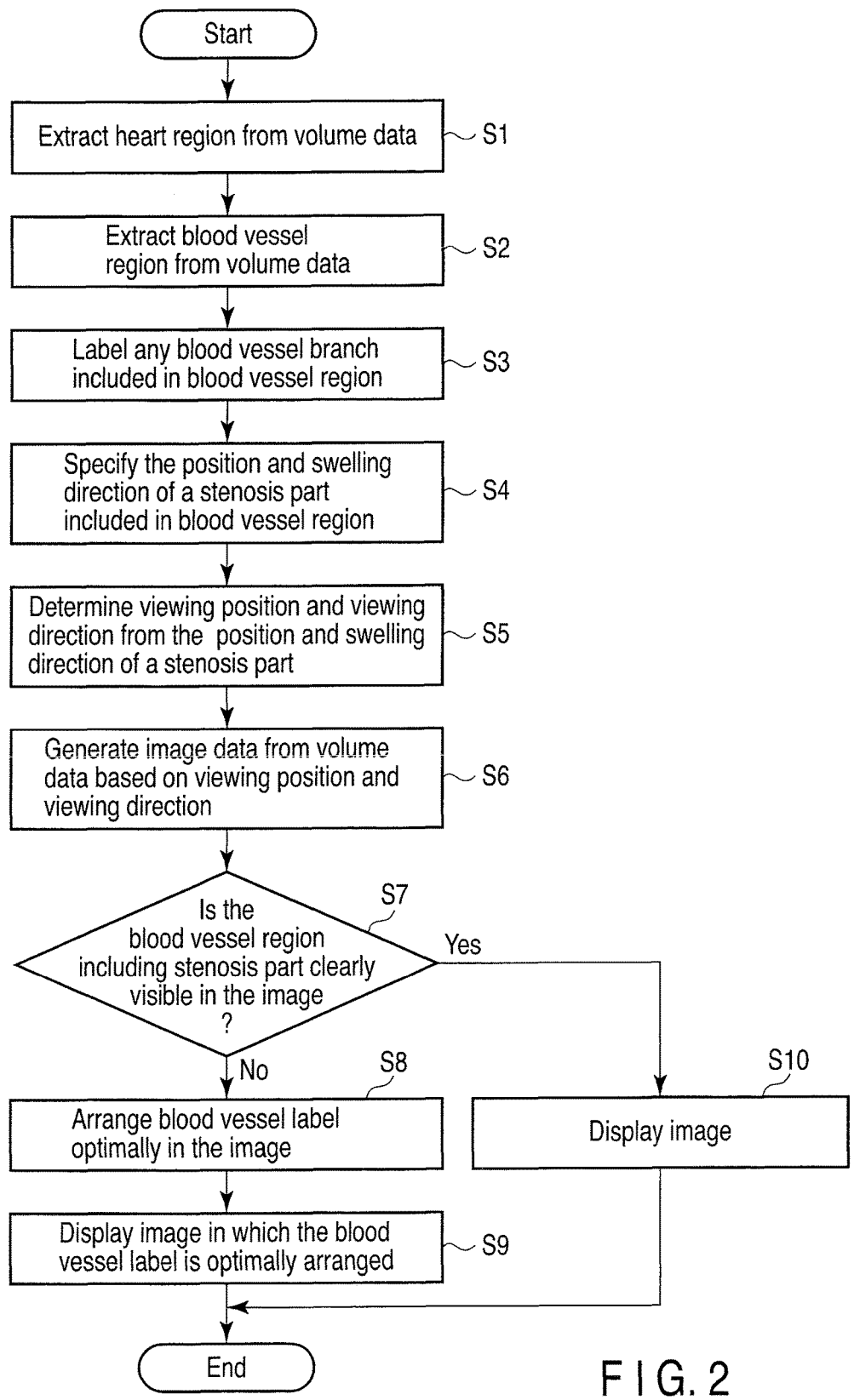
FIG. 2 is a flowchart illustrating the sequence of displaying a lesion part, under the control of the system control unit shown in FIG. 1.

FIG. 2 is a flowchart illustrating the typical sequence of displaying a lesion part, which is performed under the control of the system control unit 28.

Assume that the volume data to be processed in the optimal display process has been selected from the time-series volume data, either automatically or by operating the console unit 26. When user issues an instruction to start the optimal display process via the console unit 26, the system control unit 28 starts the optimal process of displaying the lesion part. First, the system control unit 28 causes the region extracting unit 12 to perform a process of extracting the heat region (Step S1). In Step S1, the region extracting unit 12 reads the volume data to process from the storage unit 10, and then extracts the heart region from the read volume data by using a threshold value. For example, the threshold value may set the heat region to voxel value "1," and any other region to voxel value "0." Thus, the heart region is extracted in the form of segment data. The segment data concerning the heart region is stored in the storage unit 10.

When the heart region is thus extracted, the system control unit 28 causes the region extracting unit 12 to perform a process of extracting the blood vessel region (Step 2). In Step S2, the region extracting unit 12 reads the volume data to process from the storage unit 10. The region extracting unit 12 processes the volume data, using a threshold value, extracting the blood vessel region from the volume data. The process of extracting the blood vessel region is similar to the process of extracting the heart region. That is, the volume data is processed by using the threshold value, setting the blood vessel region in the volume data, to voxel value "1," and setting any other region to voxel value "0." The blood vessel region is thus extracted in the form of segment data. The segment data about the blood vessel region extracted is stored in the storage unit 10.

After the blood vessel region has been extracted, the system control unit 28 causes the labeling unit 14 to perform a labeling process (Step S3). In Step S3, the labeling unit 14 labels the blood vessel branches included in the blood vessel region. More specifically, the labeling unit 14 first performs, for example, a skeletonization process on the blood vessel region to generate a blood vessel line. The blood vessel line in the volume data is set to voxel value "1," and any other region other than the blood vessel line is set to voxel value "0." The labeling unit 14 analyzes the structure of the blood vessel line using the position data about the blood vessel line (i.e., the coordinates of the voxel having value "1"). The blood vessel line is thereby divided into the above-mentioned blood vessel branches. The labeling unit 14 allocates the voxel of each blood vessel branch with a code corresponding to the anatomical class name (e.g., LM, LMT, LAD, LCX, or RCA, described above).

After the blood vessel branches have been labeled, the system control unit 28 causes the stenosis part specifying unit 16 to perform a stenosis part specifying process (Step S4). In Step S4, the stenosis part specifying unit 16 specifies the position and swelling direction of any stenosis part included in the blood vessel region. Various methods of specifying the position and the swelling direction are known and can be used in this field of art. The stenosis part specifying unit 16 may perform the following method to specify the position and the swelling direction, as will be described below. Note that the position and the swelling direction are specified for each blood vessel branch isolated in Step S3.

The stenosis part specifying unit 16 sets a plurality of sections (hereinafter called orthogonal sections) perpendicular to the direction in which the blood vessel line extends and spaced apart at regular intervals, in accordance with the position data pertaining to the blood vessel line and stored in the storage unit 10. A stenosis ratio is then calculated for each of the plurality of set orthogonal section. On the basis of the calculated stenosis ratio, an orthogonal section is specified, which is related to the stenosis part located on the blood vessel line. Two methods of calculating the stenosis ratio are available. In one method, the stenosis ratio is calculated from the diameter of the blood vessel. In the other method, the stenosis ratio is calculated from the section area of the blood vessel region. Either method can be used in this embodiment. The position of any orthogonal section related to the specified stenosis part is stored in the storage unit 10 as the position of the stenosis part. Hereinafter, any blood vessel branch region that includes a stenosis part will be referred to as stenosis blood vessel region.

After the position of the stenosis part has been specified, the stenosis part specifying unit 16 specifies the swelling direction of the stenosis part with respect to the orthogonal section pertaining to the stenosis part. First, the stenosis part specifying unit 16 specifies the diameter direction of the blood vessel. The specified diameter direction is related to the largest deflection parameter in the orthogonal section. More precisely, the stenosis part specifying unit 16 calculates the shortest distance from the blood vessel line in the orthogonal section to the outer wall (i.e., the inner surface of the blood vessel) of the stenosis blood vessel region. The line connecting the start point of the shortest distance (i.e., blood vessel line) and the end point thereof (i.e., inner wall of the blood vessel) extends in the direction of the diameter of the blood vessel. The direction pertains to the above-mentioned largest deflection parameter. The direction is specified as the swelling direction. The swelling direction is 3-dimensional in the volume data and represented by 3-dimensional data (e.g., XYZ orthogonal coordinates). The swelling direction is stored in the storage unit 10.

The method of specifying the position and the swelling direction of the stenosis part is not limited to the method described above. They may be calculated by the specifying unit 16, as follows. First, the stenosis part specifying unit 16 sets various diameters for blond vessels extending in different directions, respectively. These diameters are spaced apart at predetermined angular intervals. The centers of the diameters are the same and set on the blood vessel line. Next, the specifying unit 16 calculates stenosis ratios with respect to the diameters of the blood vessels. Then, the specifying unit 16 specifies the largest of the calculated stenosis ratios. Further, the stenosis part specifying unit 16 specifies the position of the orthogonal section having the largest stenosis ratio, as position of the stenosis part. In addition, the stenosis part specifying unit 16 specifies, as swelling direction, the direction of the blood vessel diameter concerning the largest stenosis ratio.

As has been described, the stenosis part is specified by image processing. The present embodiment is not limited to this, nevertheless. For example, the stenosis part may be specified by the user instruction via the console unit 26.

A plurality of stenosis parts may exist in the blood vessel region. In this case, Step S5 and the steps that follow are performed for specified stenosis part. The user may operate the console unit 26 to designate the stenosis part. Alternatively, the stenosis part having the largest stenosis ratio may be automatically designated. Further, one or more stenosis parts may be designated. In case a plurality of stenosis parts is designated, Step S5 and the steps that follow will be performed on each stenosis part.

After the position and swelling direction of each constricted part have been specified, the system control unit 28 causes the viewing position/direction determining unit 18 to determine the viewing position and the viewing direction (Step S5). In this process, the viewing position/direction determining unit 18 determines the viewing position and the viewing direction based on the position and the swelling direction of the stenosis part.

Figure 3:
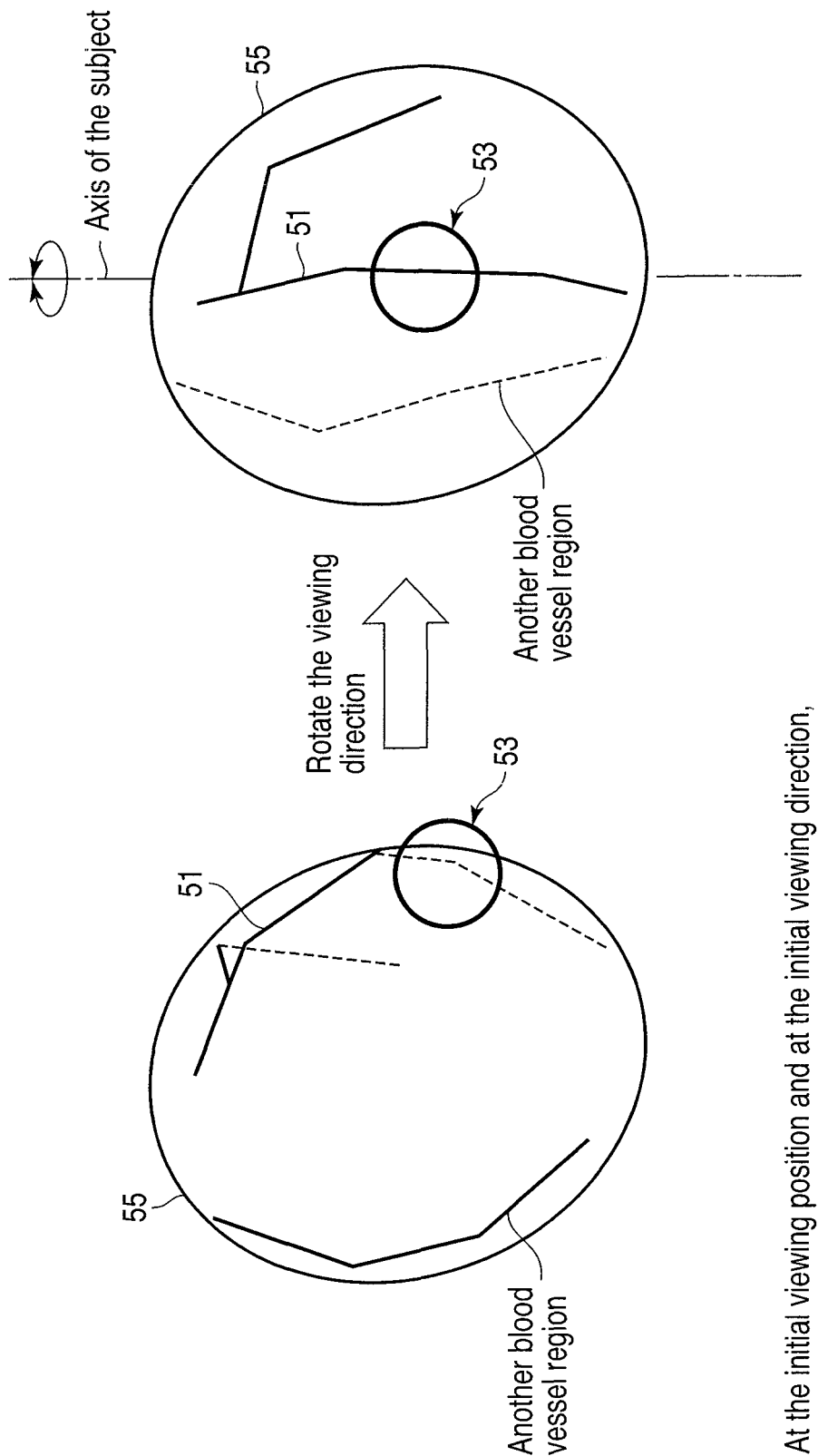
FIG. 3 is a diagram explaining Step S5 shown in FIG. 2.

The viewing direction determining process by the viewing position/direction determining unit 18 will be explained first. As shown in FIG. 3, the stenosis part 53 in the stenosis blood vessel region 51 may be positioned behind the heart region 55 or any other blood vessel region, as viewed from the initial viewing position in the viewing direction. In FIG. 3, the solid lines indicate the blood vessel region that can be seen from the viewing position, and the broken lines indicate the blood vessel region that cannot be seen from the viewing position. In this case, the viewing direction is rotated around the axis of the subject until the constricted part 53 appears almost at the midpoint in the horizontal direction of the displayed image. The angle of rotation is not limited to the above-mentioned example. The viewing direction may be rotated by a prescribed angle (for example, 180°).

Thus, the swelling state of the stenosis part may not be confirmed from the displayed image even if the viewing direction is rotated around the axis of the subject. The stenosis part looks differently on the display screen, when viewed in different directions, as will be explained with reference to FIG. 4, FIG. 5 and FIG. 6. FIG. 4 is a diagram illustrating the relation between the swelling direction and the viewing direction. FIG. 5 is a diagram illustrating an image I1 as viewed in viewing direction A shown in FIG. 4. FIG. 6 is a diagram illustrating an image I2 as viewed in viewing direction B shown in FIG. 4. Assume that as shown in FIG. 4, the stenosis part 53 in the stenosis blood vessel region swells in direction D1 that is almost parallel to the orthogonal section. Also assume that the viewing direction A is almost parallel to the orthogonal section and the swelling direction D1. Also assume that the viewing direction B is almost parallel to the orthogonal section and almost orthogonal to the swelling direction D1. Since the viewing direction A and the swelling direction D1 are parallel to each other, the user cannot confirm how a stenosis part 531 on the image I1 viewed in the viewing direction A. The stenosis part 531 is originated from the stenosis part 53. By contrast, the viewing direction B and the swelling direction D1 are almost orthogonal to each other. The user can therefore confirm how a stenosis part 532 is swelling on the image I2 viewed in the viewing direction B. The stenosis part 532 is originated from the stenosis part 53.

Thus, the more perpendicular the viewing direction is to the swelling direction, the more clearly the swelling state of the stenosis part can be displayed in the image seen in the viewing direction. The viewing position/direction determining unit 18 therefore determines that the viewing direction is perpendicular to the swelling direction.

Next, the viewing position determining process by the viewing position/direction determining unit 18 will be explained. The viewing position is set to a position where the stenosis blood vessel region lies in the image displayed. In a typical case, the viewing position is determined from the viewing direction so determined as described above and the enlargement ratio of the image.

After the viewing position and the viewing direction have been determined, the system control unit 28 causes the image generating unit 20 to perform a process of generating an image (Step S6). In Step S6, the image generating unit 20 generates image data based on the volume data in accordance with the determined viewing position and the determined viewing direction. In order to generate, for example, image data representing a CPR or SPR image, the blood vessel line of the stenosis part is used as reference curve in the CPR or SPR process.

After the image data has been generated, the system control unit 28 causes the display control unit 22 to perform a process of determining whether the image should be displayed or not (Step S7). In Step S7, the display control unit 22 determines whether a blood vessel label should be displayed in each blood vessel region displayed on the image. If almost all blood vessel branches of interest are displayed on the image, the user who knows well the position and shape of each blood vessel branch can easily identify each blood vessel branch without blood vessel label. If the user can identify the blood vessel branch with ease, however, the blood vessel label will hinder the observation of the blood vessel branch. In this case, the display control unit 22 causes the display unit 24 to display only the blood vessel label for the stenosis blood vessel. Further, the display control unit 22 determines whether the blood vessel label should be displayed or not, in accordance with the viewing state of the stenosis blood vessel region on the displayed image.

Figure 7:
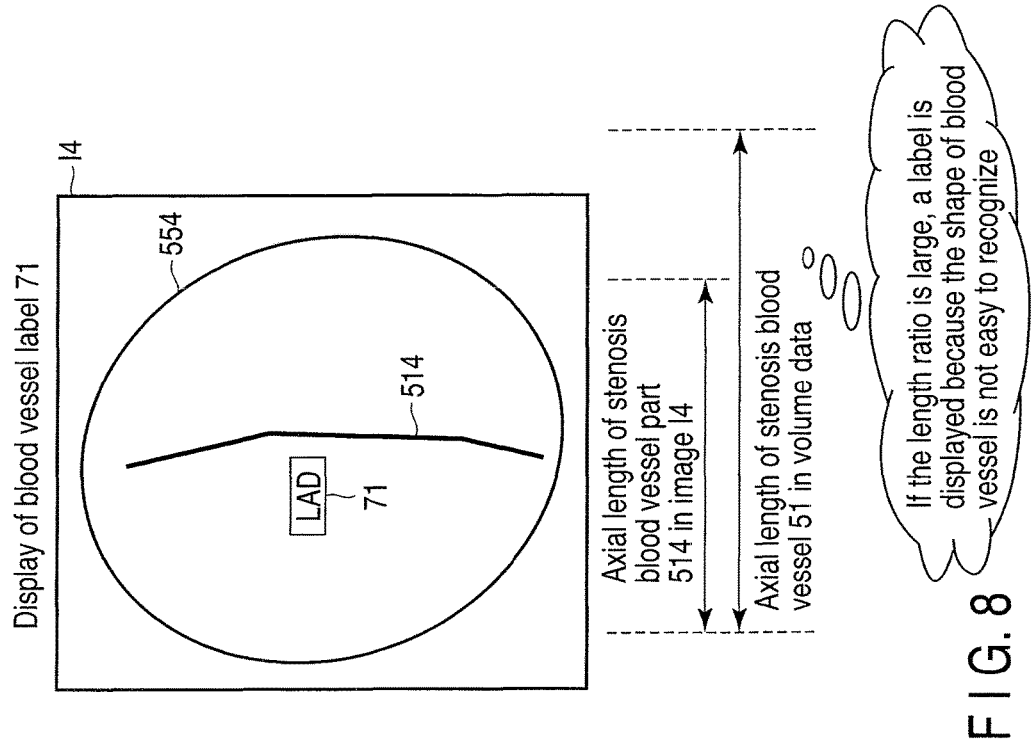
FIG. 7 is a diagram explaining Step S7 shown in FIG. 2, illustrating an image, with no blood-vessel label displayed for it.
Figure 8:
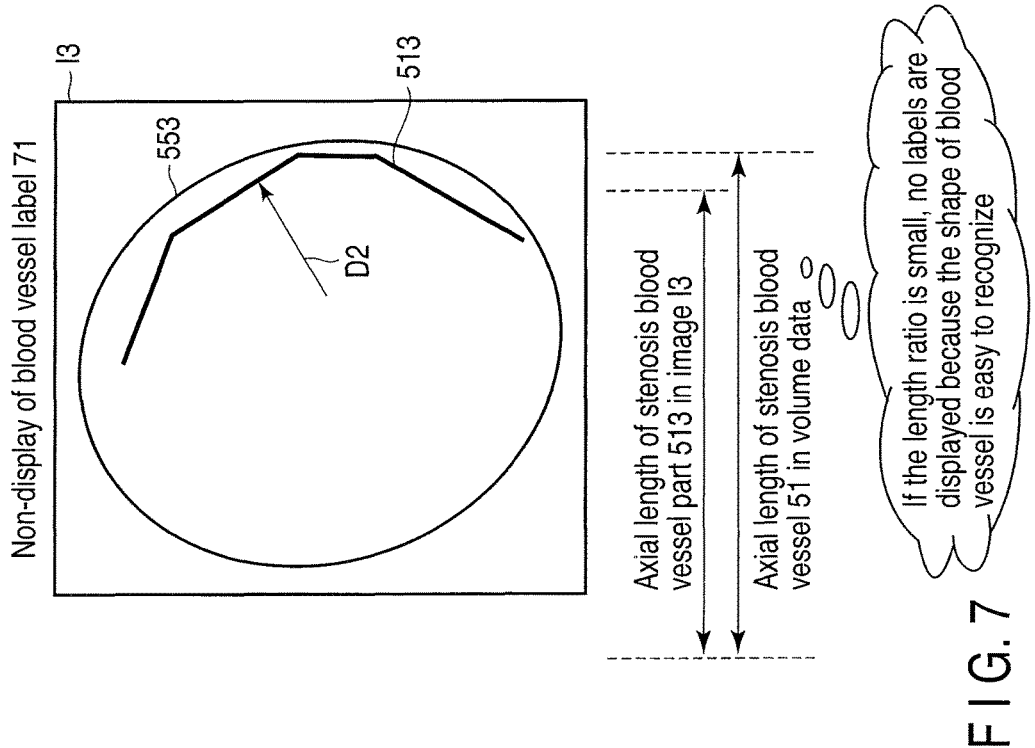
FIG. 8 is a diagram explaining Step S7 shown in FIG. 2, illustrating an image, with a blood-vessel label displayed for it.

The process the display control unit 22 performs to determine whether or not to display a blood vessel label will be explained in detail, with reference to FIG. 7 and FIG. 8. FIG. 7 is a diagram illustrating an image I3 displayed, with no blood-vessel labels displayed for it. FIG. 8 is a diagram explaining illustrating an image I4, with a blood-vessel label displayed for it. In most cases, the coronary artery is shaped like an arc, extending along the surface of the heart. The viewing direction of the image I3 is substantially perpendicular to the diameter direction D2 of this arc. The stenosis blood vessel region 513 in the image I3 is shaped like an arc. By contrast, the viewing direction of the image I4 is identical to the diameter direction D2. Hence, the stenosis blood vessel region 514 in the image I4 is not arc-shaped, but almost linear. The stenosis blood vessel region 513 in the image I3 is longer than the stenosis blood vessel region 514 in the image I4.

Therefore, the display control unit 22 determines whether a blood vessel label should be displayed for the image, in accordance with the length ratio of the stenosis blood vessel region in the image to the stenosis blood vessel region in the volume data. More precisely, in case the ratio is smaller than a threshold value, the display control unit 22 will infer that the stenosis blood vessel region is clearly displayed in the image and will determine not to display a blood vessel label. In case the ratio is larger than a threshold value, the display control unit 22 will infer that the stenosis blood vessel region is not clearly displayed in the image and will determine to display a blood vessel label. The threshold value of ratio is set to, for example, 70 to 80%. The user can set any threshold value by operating the console unit 26.

If the display control unit 22 determines that a blood vessel label should be displayed (if YES in Step S7), the system control unit 28 causes the display control unit 22 to perform a process of arranging the blood vessel label (Step S8). In Step S8, the display control unit 22 arranges the blood vessel label at an optimal position in accordance with the positional relation. The used positional relation exists between the blood vessel label and the blood vessel region on the displayed image.

Figure 9:
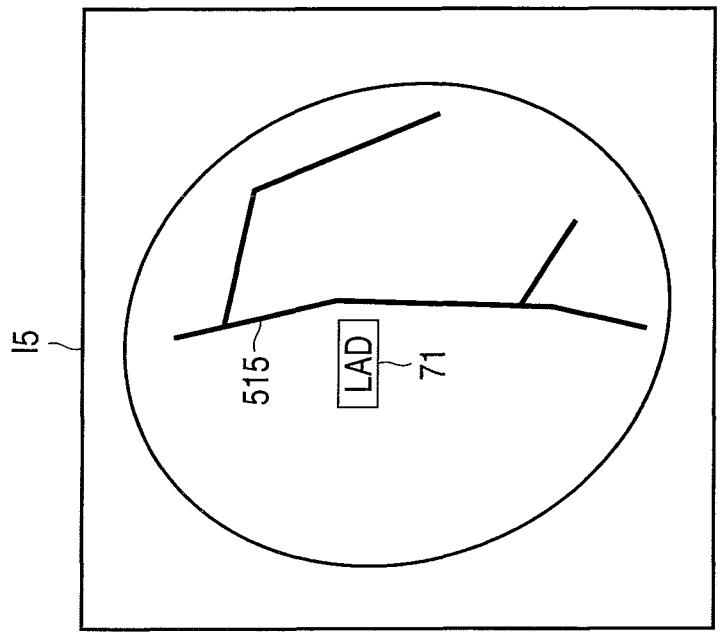
FIG. 9 is a diagram explaining Step S8 shown in FIG. 2 and also explaining the process of arranging a blood-vessel label.
Figure 9:
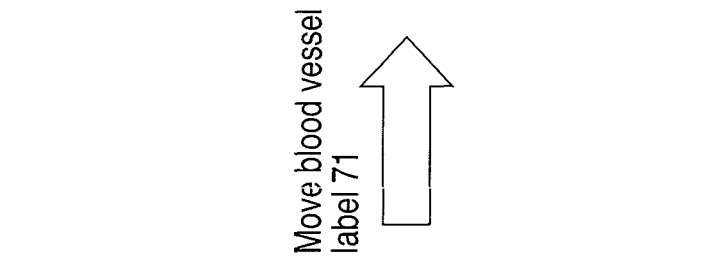
Figure 9:
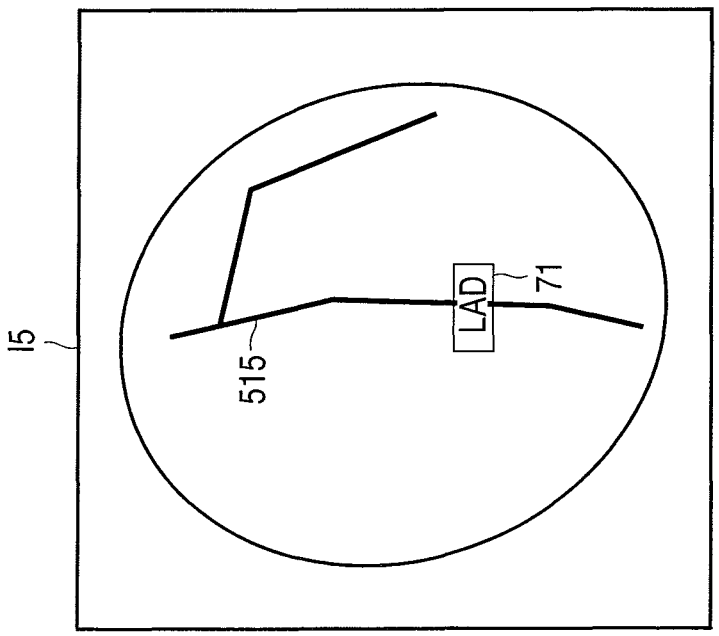

FIG. 9 is a diagram explaining the process of arranging a blood vessel label 71. As shown in FIG. 9, the blood vessel label 71 may overlap a blood vessel region such as a stenosis blood vessel region 515. If the blood vessel label 71 overlaps the blood vessel region 515, the label 71 or the region 515 will be scarcely observed. This is why the display control unit 22 arranges the blood vessel label 71 in the image I5, at a position where the label 71 does not overlap the blood vessel region 515.

A sequence of the blood vessel label arranging process will be described below. The pixels concerning the stenosis blood vessel region are set as a reference point, either automatically or manually via the console unit 26. Alternatively the pixels concerning the midpoint or one end of the blood vessel line is set as the reference point, either automatically or manually via the console unit 26. The position of the blood vessel label is provisionally set in the vicinity of the reference point. It is then determined whether the pixels concerning the blood vessel label or the pixels concerning a frame (rectangular, circular or elliptic) overlap the pixels concerning the stenosis blood vessel region or the blood vessel line. In the case of overlap, the blood vessel label is moved away until the blood vessel label becomes no longer overlapping the stenosis blood vessel region. The position without overlap is set to the final position. In the case of the no overlap, the position provisionally set is set to the final position. The data representing the final position of the blood vessel label, and the code concerning the blood vessel label are associated and stored in the storage unit 10.

If two or more blood vessel labels overlap one another, they will be rearranged not to overlap at all.

After the blood vessel label has been arranged, the system control unit 28 causes the display control unit 22 to perform a process of displaying the blood vessel label (Step S9). In Step S9, the display control unit 22 causes the display unit 24 to display an image in which the blood vessel label is arranged. To be more specific, the display control unit 22 reads the position data and code of the blood vessel label from the storage unit 10. The display control unit 22 causes to display unit 24 to superimpose the blood vessel label on the image in accordance with the read position data and code, and then to display the image and the blood vessel label.

In Step S7, the display control unit 22 may determine that a blood vessel label should not be displayed (that is, NO in Step S7). In this case, the system control unit 28 causes the display control unit 22 not to display the blood vessel label (Step S10). In Step S10, the display control unit 22 causes display unit 24 to display an image in which no blood vessel labels are arranged.

Thus, the optimal display process is completed.

As described above, in Steps S7 and S8 whether a blood vessel label should be displayed is determined in accordance with the length ratio of the stenosis blood vessel region in the image to the stenosis blood vessel region in the volume data. The embodiment is not limited to this, nevertheless. For example, at least one of the size, color and font of the blood vessel label may be changed in the image.

After the completion of the optimal display process, the user may use the displayed image in Step S9 or Step S10 to prepare a clinical report or a clinical chart. To prepare the clinical report or the clinical chart, the user performs label edition, adding other blood vessel labels, correcting the blood vessel label, or deleting the label. In this case, the display control unit 22 causes display unit 22 to display a blood-vessel label template, facilitating the edition of the blood vessel label.

Figure 10:
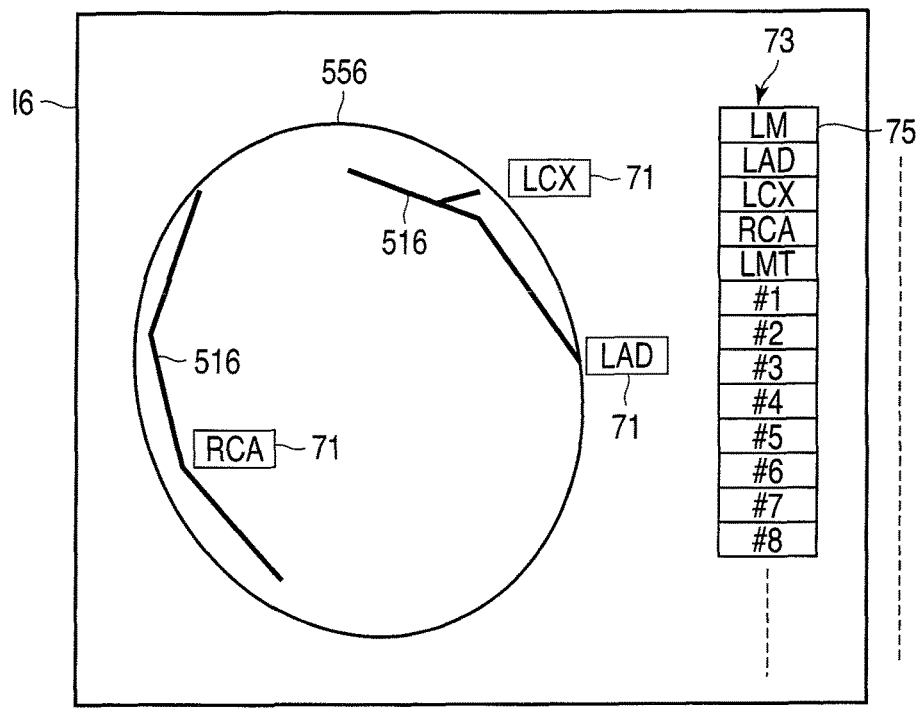
FIG. 10 is a diagram showing an exemplary blood-vessel label template, which is displayed under the control of the display control unit shown in FIG. 1.

FIG. 10 is a diagram showing an exemplary blood-vessel label template 73. The data concerning the blood-vessel label template 73 has been generated and stored in the storage unit 10. In a process of assisting the editing of the blood vessel label, the display control unit 22 reads the template 73 from the storage unit 10, and displays the template 73, as is shown in FIG. 10, at a prescribed position in the image I6. The template 73 is composed of a plurality of label templates 75 showing a plurality of class names respectively. Each of the label templates 75 can be selected via the console unit 26 by the user. A selected label templates 75 are arranged at an appropriate position in the image I6 (for example, near constricted blood vessel region 516). The appropriate position is designated by the user via the console unit 26. The label template 75 so arranged by the user is set as blood vessel label 71 and displayed. The user can set the size, shape, color etc. desirable for the blood vessel label 71 resulting from the label template 75, via the console unit 26. Moreover, the user can set size, font, color, etc. desirable for the characters included in the label, also via the console unit 26.

Figure 11:
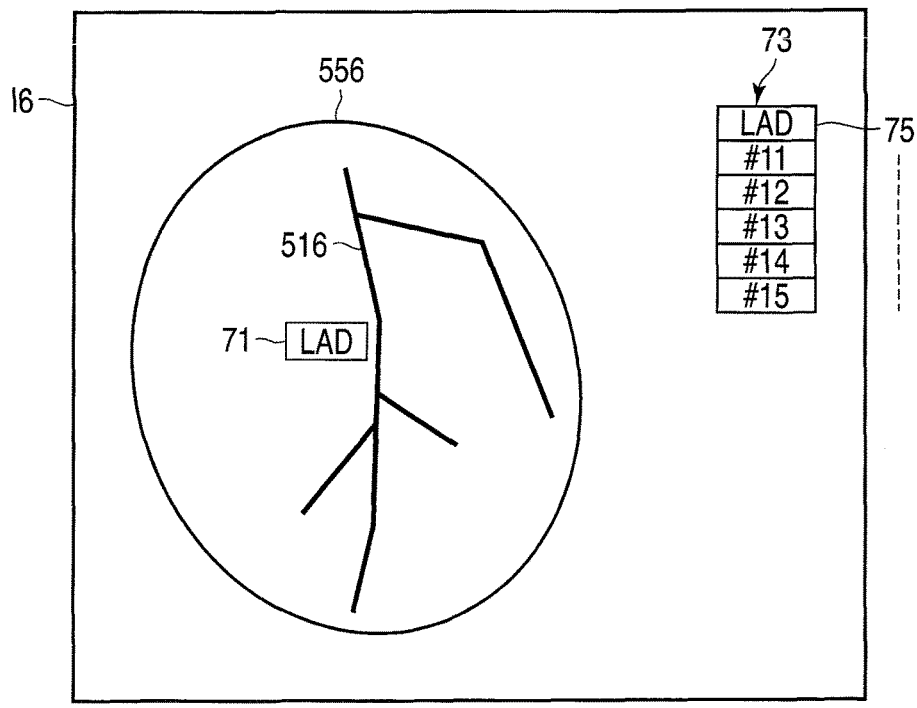
FIG. 11 is a diagram showing a different exemplary template of blood-vessel labels, which is displayed under the control of the display control unit shown in FIG. 1.

Not all label templates 75, but only the necessary templates may be read from the storage unit 10 and displayed in the image I6. FIG. 11 is a diagram showing a different exemplary template of blood-vessel labels. This template is composed of only some of the templates 75 shown in FIG. 10. The templates 75 shown in FIG. 11 pertain, for example, to the blood vessel regions downstream of the region designated by the user via the console unit 26. Further, the display control unit 22 may display only the label template 75 pertaining to the stenosis blood vessel region 516 displayed in the image I6. Alternatively, the display control unit 22 may display only the label template 75 pertaining to the stenosis blood vessel region 516 located in a mouse-cursor region that has been preset.

In the embodiment so configured as described above, the viewing position and the viewing direction, in which the shape of the blood vessel region can be easily seen, are determined from the position of the region of interest and the direction in which the blood vessel region is displaced in the region of interest. On the basis of the viewing position and viewing direction, the image data is generated. Hence, the embodiment can generate the image data from which blood vessel regions, particularly data from which the position and shape of any lesion part can be confirmed. Moreover, if only necessary blood vessel labels are displayed, the position and shape of any lesion part can be more easily determined in the image. Thus, this embodiment can provide an image processing apparatus 1 and an image processing method, both capable of increasing the efficiency of image diagnosis of the lesion parts of blood vessels.

In the embodiment described above, one image based on particular volume data is diagnosed. The invention is not to this, however. This embodiment can be applied also to the case where diagnosis is performed by display time-series image based on time-series volume data, in the form of a moving picture (so-called 4D display).

However, the blood vessel region greatly moves in the displayed image as the heart vigorously beats. As the blood vessel region expands and contracts repeatedly, it changes very much not only in shape, but also in position. Therefore, the position the blood vessel label takes in the image may change if the blood vessel label has been independently arranged in the displayed image. In case the image is displayed in this state as a moving picture, the blood vessel label will inevitably arranged at a different position. This makes it difficult for the user to recognize the label visually. To avoid this inconvenience, the display control unit 22 arranges the blood vessel label at a position optimal for displaying the image as a moving picture.

Figure 12:
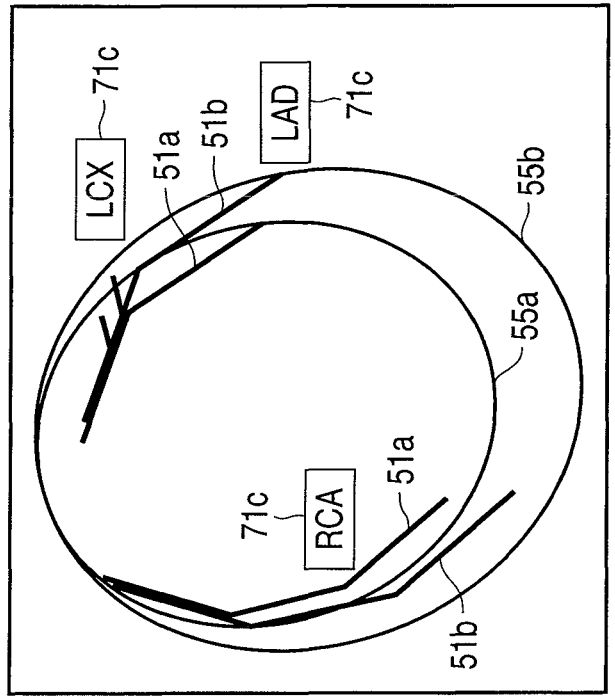
FIG. 12 is a diagram explaining a process of arranging a blood-vessel label in an image displayed as a moving picture.
Figure 12:
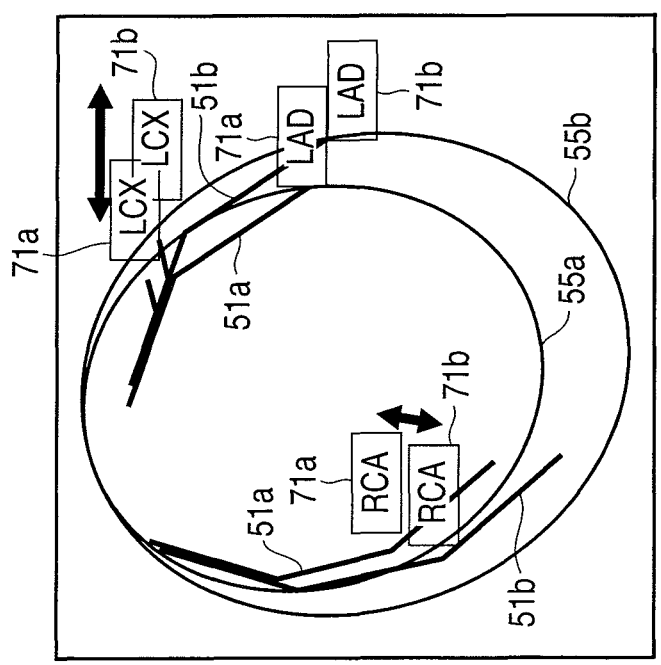

FIG. 12 is a diagram explaining a process of arranging the blood-vessel label at an optimal position in the image displayed as a moving picture. In FIG. 12, the suffix "a" indicates systole, and suffix "b" indicates diastole. As shown in FIG. 12, the blood vessel label is arranged at position 71*a* while the blood vessel region is expanding, and at position 71*b* while the blood vessel region is expanding. The optimal position for the blood vessel label is a position where the label does not move or overlap the constricted blood vessel region 71*a* or 71*b* while the image is being displayed as a moving picture. The process of arranging the blood-vessel label at the optimal position is performed in Step S8. In this process, the positions of the pixels concerning the stenosis blood vessel region 51 are determined in the image being displayed as a moving picture. Next, a position not overlapping the pixels and close to the stenosis blood vessel region 51 is determined. And a blood vessel label 71*c* is arranged at the determined position. The blood vessel label 71*c* fix at the determined position, while the image is being displayed as a moving picture.

The image processing apparatus 1 may be incorporated in a computer that diagnoses the images of lesion parts, a magnetic resonance imaging (MRI) apparatus, an ultrasonic diagnosing apparatus, a gamma camera, a single-photon emission computed tomography (SPECT) apparatus or a positron emission tomography (PET) apparatus.

The embodiment has been described on the assumption that the blood vessel is the coronary artery. Nonetheless, the embodiment can be used to diagnose the cerebral blood vessels, too, as indicated above. In regard the cerebral blood vessels, the evaluation of aneurysm is particularly important. To evaluate the aneurysm, the arteriosclerosis index may be used as deflection parameter. Then, the image diagnosing apparatus and image processing method according to this embodiment can increase the efficiency of diagnosing the images of the cerebral blood vessels.

This invention is not limited to the embodiment described above. The components of the invention can be modified in various manners in reducing the invention to practice, without departing from the sprit or scope of the invention.

Each function of the embodiment can be implemented by installing the program describing the function in a computer such as a work station and by developing the program in a memory. The program to install into the computer can be distributed in the form of a recording medium such as a magnetic disk (e.g., floppy disk, hard disk, or the like), an optical disk (e.g., CD-ROM, DVD, or the like), or a semiconductor memory.

Additional advantages and modifications will readily occur to those skilled in the art. Therefore, the invention in its broader aspects is not limited to the specific details and representative embodiment shown and described herein. Accordingly, various modifications may be made without departing from the spirit and scope of the general inventive concept as defined by the appended claims and their equivalents.

What is claimed is:

1. An image processing apparatus comprising:
a storage memory configured to store volume data including a blood vessel region;
a display; and
processing circuitry configured to:
extract the blood vessel region from the volume data stored in the storage memory;
allocate to each blood vessel branch included in the extracted blood vessel region a label indicating a class name of the blood vessel branch;
specify a position of a region of interest in the extracted blood vessel region and a deflection direction of a blood vessel region included in the region of interest based upon a deflection parameter, indicating the degree of deflection of a blood vessel wall included in the extracted blood vessel region;
determine a viewing direction so that the viewing direction is perpendicular to the deflection direction;
generate image data concerning the viewing direction based on the volume data stored in the storage memory;
display an image represented by the image data on the display;
determine whether or not the label should be displayed by comparing a length ratio between the blood vessel region included in the image displayed on the display and the blood vessel region in the volume data with a predetermined value; and
arrange, in case where the label is determined to be displayed, the label at the image displayed on the display.

2. The image processing apparatus according to claim 1, wherein the region of interest is designated by instructions of a user or by image processing.

3. The image processing apparatus according to claim 1, wherein the processing circuitry specifies the position of the region of interest and the deflection direction based on the deflection parameter, the deflection parameter being concerned with the blood vessel region included in the region of interest.

4. The image processing apparatus according to claim 3, wherein the deflection parameter is a blood vessel diameter of the blood vessel region, a blood vessel constriction rate defined as a ratio between the diameter of a normal part in the blood vessel region and the diameter of an lesion part of the blood vessel, or an arteriosclerosis index defined as a ratio between outer wall diameter and inner wall diameter of the blood vessel region.

5. The image processing apparatus according to claim 3, wherein the processing circuitry sets a plurality of sections almost orthogonal to an axis of the blood vessel region, calculates a plurality of the deflection parameters for the plurality of section, specifies the largest one of the plurality of the deflection parameters, and specifies the position of the section having the largest one of the deflection parameters, as the position of the region of interest.

6. The image processing apparatus according to claim 3, wherein the processing circuitry sets a section almost orthogonal to an axis of the blood vessel region, specifies a direction of a blood vessel diameter in the section, and specifies the direction of the blood vessel diameter as the deflection direction.

7. The image processing apparatus according to claim 1, wherein the processing circuitry changes at least one of the size, color and font of the blood vessel label, in accordance with a length ratio between the blood vessel region in the image data and the blood vessel region in the volume data.

8. The image processing apparatus according to claim 1, wherein the processing circuitry changes at least one of the size, color and font of the blood vessel label in accordance with a positional relation, the positional relation being existed between the blood vessel label and the blood vessel region in the image data.

9. The image processing apparatus according to claim 8, wherein the display displays the label in fixed state in order to display a time-series image based time-series volume data.

10. An image processing method carried out by processing circuitry, the method comprising:
    extracting a blood vessel region from volume data stored in a storage device;
    allocating to each blood vessel branch included in the extracted blood vessel region a label indicating a class name of the blood vessel branch;
    specifying a position of a region of interest in the extracted blood vessel region and a deflection direction of a blood vessel region included in the region of interest based upon a deflection parameter, indicating the degree of deflection of a blood vessel wall included in the extracted blood vessel region;
    determining a viewing direction so that the viewing direction is perpendicular to the deflection direction;
    generating image data concerning the viewing direction based on the volume data stored in the storage memory;
    displaying an image represented by the image data on a display;
    determining whether or not the label should be displayed by comparing a length ratio between the blood vessel region included in the image displayed on the display and the blood vessel region in the volume data with a predetermined value; and
    arranging, in case where the label is determined to be displayed, the label at the image displayed on the display.

11. The image processing method according to claim 10, wherein the region of interest is designated by instructions of a user or by image processing.

12. The image processing method according to claim 10, wherein the position of the region of interest and the deflection direction are identified on the basis of the deflection parameter, the deflection parameter being concerned with the blood vessel region included in the region of interest.

13. The image processing method according to claim 12, wherein the deflection parameter is a blood vessel diameter of the blood vessel region, a blood vessel stenosis rate defined as a ratio between the diameter of a normal part in the blood vessel region and the diameter of an lesion part of the blood vessel, or an arteriosclerosis index defined as a ratio between outer wall diameter and inner wall diameter of the blood vessel region.

14. The image processing method according to claim 12, wherein a plurality of sections almost orthogonal to an axis of the blood vessel region are set, a plurality of the deflection parameters is calculated for the plurality of section, the largest one of the plurality of the deflection parameters is specified, and the position of the section having the largest one of the deflection parameters is specified as the position of the region of interest.

15. The image processing method according to claim 12, wherein a section almost orthogonal to an axis of the blood vessel region is set, a direction of a blood vessel diameter in the section is set, and the direction of the blood vessel diameter is specified as the deflection direction.

16. The image processing method according to claim 10, further comprising changing at least one of the size, color and font of the blood vessel label, in accordance with a length ratio between the blood vessel region in the image data and the blood vessel region in the volume data.

17. The image processing method according to claim 10, further comprising changing at least one of the size, color and font of the blood vessel label in accordance with a positional relation, the positional relation being existed between the blood vessel label and the blood vessel region in the image data.

18. The image processing method according to claim 17, wherein the label is displayed in fixed state in order to display a time-series image based time-series volume data.

* * * * *